United States Patent [19]

Swain

[11] Patent Number: 5,409,691

[45] Date of Patent: Apr. 25, 1995

[54] SOLUTION COMPRISING ALUMINUM ACETATE AND GLYCERIN

[76] Inventor: Dan E. Swain, 301 S. Highland Ave., No. 902, Pittsburgh, Pa. 15206

[21] Appl. No.: 138,669

[22] Filed: Oct. 18, 1993

[51] Int. Cl.$^6$ .......................... A61K 7/16; A61K 33/06
[52] U.S. Cl. ........................................ 424/49; 424/58; 424/682; 424/698; 514/827; 514/828; 514/848; 514/861; 514/862; 514/865; 514/886; 514/887; 514/901; 514/928
[58] Field of Search .................... 424/49–58, 424/682, 698; 514/827, 828, 848, 861, 862, 865, 886, 887, 901, 928

[56] References Cited

U.S. PATENT DOCUMENTS

| | | |
|---|---|---|
| 3,856,941 | 12/1974 | Turner ............................ 424/145 |
| 4,146,605 | 3/1979 | Ritchey . |
| 4,277,463 | 7/1981 | Tomic ............................ 424/128 |
| 4,346,709 | 8/1982 | Schmitt . |
| 4,438,100 | 3/1984 | Balslev et al. . |
| 4,537,689 | 8/1985 | Morrow et al. . |
| 4,618,491 | 10/1986 | Kanematu et al. .............. 424/81 |
| 4,784,908 | 11/1988 | Ungar et al. . |
| 4,840,798 | 6/1989 | Skaliotis ....................... 424/488 |
| 4,879,116 | 11/1989 | Fox et al. ...................... 424/682 |
| 4,895,727 | 1/1990 | Allen . |
| 4,906,455 | 3/1990 | Hoerman . |
| 4,938,963 | 7/1990 | Parnell . |
| 4,940,056 | 7/1990 | Heck et al. . |
| 4,963,591 | 10/1990 | Fourman et al. . |
| 4,976,954 | 12/1990 | Kleber et al. .................. 424/52 |
| 4,980,177 | 12/1990 | Cherukuri et al. . |
| 4,983,378 | 1/1991 | Parnell . |
| 4,997,654 | 3/1991 | Corsello et al. . |
| 5,006,571 | 4/1991 | Kumar et al. . |
| 5,015,474 | 5/1991 | Parnell . |
| 5,028,412 | 7/1991 | Putt et al. ...................... 424/48 |
| 5,032,115 | 7/1991 | Hakansson et al. . |
| 5,064,640 | 11/1991 | Kleber et al. .................. 424/52 |
| 5,082,660 | 1/1992 | Ounanian et al. . |
| 5,098,719 | 3/1993 | Anderson et al. ............... 426/2 |
| 5,116,621 | 5/1992 | Oji et al. . |
| 5,147,648 | 9/1992 | Bannert . |
| 5,158,772 | 10/1992 | Davis . |
| 5,200,211 | 4/1993 | Anderson et al. ............... 426/2 |
| 5,234,915 | 8/1993 | Mathur et al. ................. 514/57 |

FOREIGN PATENT DOCUMENTS

| | | |
|---|---|---|
| 3421443 | 12/1985 | Germany . |
| 59-007113 | 1/1984 | Japan . |
| 59-013718 | 1/1984 | Japan . |
| 59-108045 | 6/1984 | Japan . |
| 60-025936 | 2/1985 | Japan . |
| 60-099180 | 6/1985 | Japan . |

OTHER PUBLICATIONS

Gouth EP 100447 (Feb. 15, 1984).
Daice Chem JP 61259750 (Nov. 18, 1986).
Nitto Electric JP 61260014 (Nov. 18, 1986).
Teikoku Seiyaku JP 04178323 (Jun. 25, 1992).
Toko Yakuhin JP 05092920 (Apr. 16, 1993) C.A. 119:167825.
Nippon Junyaeu JP 06128151 (May 10, 1994).
Fed. Regist. 55(119): 25204–32 20 Jun. 1990 GA. 113:84672.
Szendrei et al HV 4627 (Oct. 28, 1988) C.A. 111:140584.
Hanashi Jpn 55017347 (Feb. 6, 1980) C.A. 93:137991.

Primary Examiner—Shep K. Rose
Attorney, Agent, or Firm—Paul D. Bangor, Jr.; Michael J. Kline

[57] ABSTRACT

Solution comprising a mixture of aluminum acetate topical solution and glycerin useful as a skin moisturizer and/or a food particulate repellant for preventing chewed food particles from sticking to the teeth. When combined with a flavoring agent, the solution of aluminum acetate topical solution and glycerin is also effective as a saliva substitute for relieving the symptoms of xerostomia or "dry mouth syndrome."

29 Claims, No Drawings

SOLUTION COMPRISING ALUMINUM ACETATE AND GLYCERIN

TECHNICAL FIELD

The present invention relates to a solution comprising a topical solution of aluminum acetate and glycerin as the active ingredients.

BACKGROUND OF THE INVENTION

The solution of the present invention has at least three applications. The solution of the present invention may be used as a moisturizer and sprayed or otherwise applied to the area of the body frequently covered by a diaper or other such type of undergarment worn, for example, by an incontinent, for effectively preventing irritations of the skin such as dermatitis, bed sores and the like.

Additionally, the solution of the present invention may be applied to the teeth and dental work to effectively retard chewed food particulates from sticking thereto. As a result, the solution of the present invention aids in the prevention of dental caries.

Furthermore, when combined with a flavoring agent, the solution is an effective saliva substitute for alleviating the symptoms of xerostomia, commonly known as "dry mouth syndrome."

Xerostomia is a condition in which the salivary glands produce insufficient quantities of saliva. Lack of sufficient saliva causes discomfort which can, in some cases, be quite severe. Without saliva, the mouth burns and the throat and tongue can undergo radical changes. Teeth can decay rapidity and the tongue can become smooth, cracked and vulnerable to infection. Often, there is a loss of taste, and because saliva contains important digestive enzymes, there are often problems with digestion.

The mouth is one of the body areas most exposed to the external environment. Normally, mucous forms a continuous protective layer in the nose, mouth and throat. A patient suffering from xerostomia not only has decreased fluid in the mouth, but also an insufficient quantity of mucoproteins and mucopolysaccharides to hold fluid in contact with the cells and create a barrier to irritation and infection.

Cases of xerostomia may vary from mild, in which only slight dryness is experienced, to severe cases in which the patient will have serious problems with mastication, swallowing, digestion, speech, tooth decay, and the like. As noted in U.S. Pat. No. 4,438,100 to Balslev, et al., there are a number of causes of xerostomia, including the physiological (e.g., age, menopause, post-operative conditions, dehydration), as well as the psychic (nervousness). The reasons for mouth dryness may also be pharmacological (e.g., as a common side effect of many medications, including diuretics, antiarthritics, anticholinergics, anti-depressants, and oral inhalers). Because such medicaments are not curative but are used for long-term treatment, the dry-mouth side effect is long-term as well.

Anti-cholinergics act on the vagus nerve and their actions are readily predictable by considering the consequence of interruption of parasympathetic and sympathetic cholinergic nerve stimulation. These consequences include: decreased gastro-intestinal motility, decreased gastric secretion, dry-mouth, and drying of mucous membranes in general, etc. Thirst and difficulty in swallowing occur when the mouth and esophagus become sufficiently dry, and dry-mouth fosters oral ulcerations and dental caries. It appears the most logical treatment for the "drying" side effects would by symptomatic, and non-systemic. Systemic medications would be irregularly absorbed since the primary agent (anticholinergic) acts to retard gastric emptying.

Oral inhalers, although not necessarily anticholinergic, present a similar side effect profile. The constant pounding, especially by elderly or inexperienced users, of the aerosolized powder against the throat causes undue dryness of the oral cavity. The non-systemic pathway discussed above has proven beneficial here as well since this condition has been heretofore left largely untreated.

Parkinson's disease, chronic or acute diarrhea, and anti-cholinergic preparations to treat ulcers, colitis, irritable bowel syndrome, etc., also commonly cause dry-mouth as a side effect. Xerostomia may also result from radiotherapy. The most severe cases of xerostomia are caused by radiation therapy after head and neck surgery and by autoimmune diseases such as lupus, Sjogrens Syndrome, and rheumatoid arthritis. See, for example, P. C. Fox, et al., *J. Am. Dental Assoc.* 110:519–525 (1985).

Until recently, the treatments for xerostomia have had significant drawbacks. For example, symptoms of mild xerostomia can be somewhat alleviated by consumption of fluids, hard candy and throat lozenges. Because of the susceptibility of xerostomia patients to tooth decay and gum disease, however, the increased sugar intake associated with conventional candy and lozenges is likely to further accelerate tooth decay and/or gum disease in an affected patient. In addition, fluids or candy are typically not effective with more severe cases of xerostomia, nor do they provide long-lasting relief for even mild cases.

There are also a number of artificial salivas on the market which contain alcohol, mineral oils, glycerine, and combinations of polyethylene glycols. A number carboxymethylcellulose-base preparations are on the market as well, including those sold under the marks Orex ® (Young Dental), Xero-Lube ® (Scherer), MoiStir ® (Kingswood Laboratories), and Salivart ® (Westport Pharmaceuticals). Many patients find, however, that such preparations are irritating or distasteful, and that their lubricating effect is of relatively short duration.

There has also been some experimentation with para-sympathomimetic drugs, i.e., drugs that mimic the action of the parasympathetic nervous system which controls salivation. There have been reported dosage control problems with these drugs; however, as well as significant side effects.

DESCRIPTION OF THE PRIOR ART

U.S. Pat. Nos.: 5,064,640 and 4,976,954 both to Kleber et al., disclose anticariogenic oral preparations (such as mouthwashes, dentifrice, lozenges and chewing gum) comprising water-soluble aluminum salts in an amount sufficient to provide an anticariogenic concentration of aluminum ions in an aqueous emulsion stabilized with selected surfactants, and including one or more substances selected from flavor oils, humectants, and sweeteners. The Kleber patents teach that the particular water-soluble aluminum salt employed is not critical and that any non-toxic, water-soluble aluminum ion-containing salt may be used, including aluminum acetate. The preferred humectant in the emulsion taught by the Kleber patents is glycerin. The Kleber patents further teach that humectant materials are present in the emulsion thereof in an amount ranging from about 1 to about 90 percent by weight, preferably about 5 to about 60 percent by weight, and more preferably about 5 to about 20 percent by weight. In the mouthwash formulations taught by the Kleber patents, the humectant material typically comprises about 10 percent by weight of the formulation.

U.S. Pat. No. 5,08,412 to Putt et al., discloses a calculus inhibiting oral composition comprising an aqueous aluminum-carboxylic acid complex and a carrier suitable for use in the oral cavity, such carrier including cleaning and polishing agents, chewing gum bases and humectants (such as glycerin). Aluminum acetate is disclosed by the Putt patent to be a suitable aluminum salt for providing the aluminum ions in solution necessary for the formation of the anti-calculus carboxylate complex. The aluminum-carboxylate complexes are provided in the oral compositions of the Putt patent at a level greater than 0 up to about 25 percent by weight of the oral composition. Increasing the amounts of the complexes to higher levels is limited by their solubility and by taste considerations.

U.S. Pat. No. 4,438,100 to Balslev et al., discloses a viscous artificial saliva containing a mucine and an oxidizing bacteriocide.

U.S. Pat. No. 4,209,505 to Mikhail discloses a mouthwash for dry mouth relief containing pilocarpine or a pilocarpine derivative. It is also noted therein that various types of diets have been used (albeit unsuccessfully) in an attempt to alleviate xerostomia.

U.S. Pat. No. 4,151,270 to Ream et al., teaches a chewing gum composition formulated to stimulate salivation. The gum contains fructose and an organic acid such as adipic, ascorbic, citric, fumaric, lactic or tartaric acids.

U.S. Pat. Nos.: 4,938,963 and 4,983,378, both to Parnell, teach a composition and method for alleviating xerostomia. The compositions of the Parnell Patents comprise a Yerba Santa extract (eriodictyon fluid) and a sweetener, and may be an aqueous solution or in gum or lozenge form. The compositions may additionally contain a stimulator compound effective to stimulate salivary gland secretion, e.g., citric acid, ascorbic acid or both. Preservatives, flavoring agents, coloring agents, emulsifiers, and the like may be included in the compositions as well.

U.S. Pat. No. 5,116,621 to Oji, et al., teaches an anti-inflammatory analgesic patch having a drug reservoir layer comprising 4-biphenylylacetic acid as the effective ingredient, a homo- and/or co-polymer of acrylic acid and ordinary adjuvants such as a shape-retaining agent, humectant, thickener, etc., which is characterized in that the drug reservoir further contains crotamiton and the pH of the drug reservoir is adjusted within a range of 6 to 8 with a water-soluble organic amine and an organic acid. Glycerin (13.21% to 17.13% by weight) is one of the humectants disclosed inn the specific examples of the compositions taught by the Oji Patent and aluminum acetate is disclosed as being one of the adjuvants, among many others, contained in one such example. The Oji Patent further teaches that the preferred amount of the humectant or humectants of the composition ranges from about 10% to 60% by weight and more preferably from 20% to 50% by weight, based on the weight of the drug reservoir.

U.S. Pat. No. 4,997,654 to Corsello, et al., teaches a method for increasing salivation as a treatment for xerostomia which comprises chewing gum or candy containing from 4% to 70% by weight xylitol.

U.S. Pat. No. 4,537,689 to Morrow, et al., discloses an oral lubricant effective in reducing the discomfort associated with the wearing of a mouth protector during periods of activity consisting essentially of a lubricating agent such as glycerine, a thickening agent, a preservative, a flavoring agent, a sweetener, an emulsifier, if needed, and a diluent.

U.S. Pat. No. 5,147,648 to Bannert teaches a method of treating xerostomia with a gel having an improved adhesiveness to the oral mucosa of a human patient, comprising first applying to the oral mucosa of the patient an aqueous solution of a calcium salt which is capable of forming a gel with a polysaccharide, where the calcium salt solution has a concentration of 0.01 to 50 mMols of calcium per 100 mL, and subsequently applying to the thus treated oral mucosa of the patient an aqueous solution of a polysaccharide selected from the group consisting of sodium alginate and pectin, where the polysaccharide solution contains 0.01% to 12.5% by weight of polysaccharide.

SUMMARY OF THE INVENTION

The present invention comprises a solution of aluminum acetate topical solution and glycerin, which may include an additional flavoring agent. In general, the solution of the present invention preferably comprises from about 40 vol. % to about 61 vol. % aluminum acetate topical solution and from about 39 vol. % to about 60 vol. % glycerin. In terms of weight percentages, the solution of the present invention comprises from about 28 wt. % to about 50 wt. % aluminum acetate topical solution and from about 50 wt. % to about 72 wt. % glycerin.

When present, the flavoring agent or agents will be present in an amount depending on the individual agent(s) selected, but, if present, will preferably be in the range of about 1 vol. % to about 21 vol. %, more preferably about 2 vol. % to about 6 vol. %, and most preferably about 2 vol. % of the solution. The preferred flavoring agent is a lemon extract which, in addition to providing flavor to the solution, also acts to stimulate natural salivation. In terms of weight percentages, the flavoring agent preferably comprises from about 1 wt. % to about 19 wt. %, more preferably from about 2 wt. % to about 6 wt. %, and most preferably about 2 wt. % of the solution.

It is a primary object of the present invention to provide a solution containing an aluminum acetate topical solution and glycerin which has various uses.

It is another object of the present invention to provide a solution containing an aluminum acetate topical solution and glycerin useful for preventing irritations to areas of the skin that are frequently covered by a diaper or other such type of undergarment.

It is yet an additional object of the present invention to provide a solution containing an aluminum acetate topical solution and glycerin useful as a food particulate repellant which, when applied to the teeth before meals, effectively inhibits chewed food particulates from sticking to the teeth.

It is yet a further object of the present invention to provide a clear solution useful as a saliva substitute for treating xerostomia which contains a topical solution of aluminum acetate, glycerin and a flavoring agent.

It is yet a further object of the present invention to provide a solution useful as a saliva substitute for treating xerostomia which contains a topical solution of aluminum acetate, glycerin and a flavoring agent, such as lemon extract (or other source of citric acid), which acts to stimulate salivary gland secretion.

These and other features and advantages of the preferred embodiments of the present invention will become readily apparent from the following detailed description of the preferred embodiments and claims.

DETAILED DESCRIPTION OF THE PREFERRED EMBODIMENTS

The solution of the present invention combines glycerin, a long-acting oral moisturizer, with an aluminum acetate topical solution known for its anti-infective properties. Neither of the components is significantly absorbed into the bloodstream, thereby producing its effects locally and non-systematically. The moisturizing entity, glycerin, is a useful humectant, with an agreeable taste and high viscosity. This component has the known ability to dissolve vegetable acids and pepsin, which may play a role in neutralizing oral ulcers caused by excess acidity or gastric reflex when the solution is used as a saliva substitute.

The second component of the solution of the present invention, an aluminum acetate topical solution, is a protein precipitant with astringent and anti-septic action. As prescribed in United States Pharmacopeia XXII, the aluminum acetate topical solution yields, from each 100 mL, not less than 1.20 g and not more than 1.45 g of aluminum oxide ($Al_2O_3$), and not less than 4.24 g and not more than 5.12 g acetic acid ($C_2H_4O_2$), corresponding to not less than 4.8 g and not more than 5.8 g of aluminum acetate ($C_6H_9AlO_6$). Aluminum acetate topical solution may be stabilized by the addition of not more than 0.6 percent of Boric Acid. The aluminum acetate topical solution is made by mixing 545 mL of aluminum subacetate topical solution, 15 mL of glacial acetic acid, and a sufficient quantity of purified water to make 1000 mL of the solution. The solution is mixed and filtered, if necessary, to produce a clear aluminum acetate topical solution.

As also prescribed in United States Pharmacopeia XXII, aluminum subacetate topical solution is produced by dissolving 145 g of aluminum sulfate in 600 mL of cold, purified water, filtering the resulting solution and then gradually adding 70 g of precipitated calcium carbonate, in several portions with constant stirring. Acetic acid, 160 mL, is then slowly added to the solution and mixed. The mixture is then set aside for 24 hours. The product is then filtered, with the aid of a vacuum if necessary, returning the first portion of the filtrate to the funnel. The magma on the filter is then washed with small portions of cold, purified water until the total filtrate measures 1000 mL which comprises the aluminum subacetate topical solution.

The aluminum acetate topical solution has a very low viscosity and consequently such a low cell permeability that its action is limited to the local (non-systemic) cell surface. If used alone as a saliva substitute, aluminum acetate topical solution would tend to offset mucous secretion and the effected area would become dryer. However, in combination with glycerin, it appears to allow for the contracting (astringent-like) action of tissues, so as to force and hold the glycerin in place. The antiseptic action of the aluminum acetate topical solution enables the solution, when used as a saliva substitute, to retard formation of mouth ulcerations, dental caries and bacteria formally kept in check by adequate salivary output.

In general, the solution of the present invention preferably comprises from about 40 vol. % to about 61 vol. % aluminum acetate topical solution and from about 39 vol. % to about 60 vol. % glycerin. In terms of weight percentages, the solution of the present invention comprises from about 28 wt. % to about 50 wt. % aluminum acetate topical solution and from about 50 wt. % to about 72 wt. % glycerin In a preferred embodiment of the solution useful as a skin protectant, the solution comprises a mixture of aluminum acetate topical solution and glycerin. The solution of this embodiment will preferably comprise a mixture of equal volumes of aluminum acetate topical solution and glycerin in liquid form. As an example, approximately eight ounces of the solution can be made by mixing 120 mL of aluminum acetate topical solution with 120 mL of glycerin. The solution of this embodiment of the present invention useful as a skin protectant, however, may preferably contain in the range from about 45 vol. % to about 55 vol. % aluminum acetate topical solution and from about 45 vol. % to about 55 vol. % glycerin. In terms of weight percentages, the solution of this preferred embodiment comprises from about 55 wt. % to about 66 wt. % glycerin and from about 34 wt. % to about 45 wt. % aluminum acetate topical solution. Most preferably, the solution of this preferred embodiment comprises from about 60 wt. % to about 63 wt. % glycerin and from about 37 wt. % to about 40 wt. % aluminum acetate topical solution.

When used as a skin protectant, the solution of the present invention is preferably sprayed from a pump bottle onto the areas of the skin frequently covered for prolonged periods of time by a diaper or other such garment. The skin treatment of the present invention provides a barrier between the skin and excrements trapped by the diaper and thereby prevents such excrements from causing irritations of the skin.

In a further preferred embodiment, the solution of the present invention useful as a particulate repellant comprises a solution of about 60 vol. % glycerin and about 40 vol. % aluminum acetate topical solution. In terms of weight percentages, the solution of this preferred embodiment effective as a particulate repellant comprises a solution from about 69 wt. % to about 72 wt. % glycerin and from about 28 wt. % to about 31 wt. % aluminum acetate topical solution.

The particulate repellant comprising 60 vol. % glycerin and 40 vol. % aluminum acetate topical solution of the present invention effectively adheres to dental surfaces without incident and acts to repel food particulates that would otherwise cling to those dental surfaces. Such particulate repellant is safe, non-toxic and non-systematically active if ingested. Further, such particulate repellant (1) is palatable, (2) does not leave a visible residue on the teeth, and (3) lasts for at least thirty minutes to effectively repel food particulates during the time taken to eat a normal meal.

IN-VITRO TESTING OF THE PARTICULATE REPELLANT

A sample size of approximately one teaspoonful, weighing 2 grams, of Lipton Noodle Soup, freeze-dried and lightly triturated, was used as the food sample for testing a control substance, water, to be compared to the particulate repellant of the present invention. A sample dental material comprising a semi-flexible, non-porous plastic strip of about 6 inches in length and ⅛ inches thick was lightly coated with water to simulate normal saliva. The water was not absorbed by the plastic. Instead, the water beaded on the surface of the plastic in a similar manner to the beading of water or saliva on human teeth.

The food sample was sprinkled across the dental material and a porcelain pestle was used to triturate the food sample against the dental material to simulate chewing. As in human ingestion, water on the dental material was taken up by the food sample, which became a sticky mess and remained on the plastic dental material. Rinsing the dental material incompletely removed the food particles. Physical means, other than rinsing, was required to remove the sticky food particles from the dental material.

To test the effectiveness of the particulate repellant comprising 60 vol. % glycerin and 40 vol. % aluminum acetate topical solution of the present invention, an identical 2 gram food sample was ground against an identical plastic dental material which had been lightly coated with the particulate repellant. The 2 gram food sample was sprinkled onto the coated plastic dental material and triturated to resemble chewing as in the control testing described above. A sticky complex of the food sample and particulate repellant comprising 60 vol. % glycerin and 40 vol. % aluminum acetate topical solution was formed on the dental material. On visual examination, however, it was seen that such particulate repellant present on the dental material was not sufficiently absorbed by the food sample, in comparison to the control test. In this case, only water was necessary to rinse clean the plastic dental material. The complex formed in the test of the particulate repellant comprising 60 vol. % glycerin and 40 vol. % aluminum acetate topical solution rinsed cleanly and did not form a semi-dissolved, glue-like substance as did the water/food complex in the control test.

In addition, a food solubility test was performed to compare the solubility of the food sample when immersed in water (used to simulate saliva) and in the particulate repellant of the present invention comprising 60 vol. % glycerin and 40 vol. % aluminum acetate topical solution.

After one hour, the food samples in the water and in the particulate repellant comprising 60 vol. % glycerin and 40 vol. % aluminum acetate topical solution exhibited obvious physical differences. The food sample in water had swelled under the excess hydration and became very sticky. Further, the integrity and color of the water had drastically changed. To the contrary, the other food sample had absorbed very little of the particulate repellant. Even after one hour, the food sample in immersed the particulate repellant remained in tact. This latter food sample did not congeal and the integrity and color of the particulate repellant remained consistent. The addition of 5 mL of water produced no noticeable effect. The addition of another 5 mL (10 mL total) of water changed the integrity/color of the particulate repellant comprising 60 vol. % glycerin and 40 vol. % aluminum acetate topical solution, but no additional hydration of the food sample occurred. Even after another 10 mL of water was added (20 mL total), no excess hydration or swelling of the food sample occurred. On the contrary, it appeared that a binding force protected the food sample, as a noticeable ring encompassed the food sample and such ring appeared to shield the food sample as water was added.

These tests show that the particulate repellant of the present invention comprising 60 vol. % glycerin and 40 vol. % aluminum acetate topical solution not only binds to the dental material, but also to the food particles themselves. The binding of such particulate repellant to the food particles is significant in that this prevents their uptake of water which, under normal conditions, "glues" the particles to the teeth. A viscous coating of such particulate repellant remains on the teeth and gravity alone will most likely prevent the food particles from adhering thereto. Should the food particles adhere to the dental surfaces, they will bind to the particulate repellant. The binding will not change the clear, transparent integrity of the particulate repellant and the addition of water will force the food particles to slide away much faster than they would had the particulate repellant not been applied.

Thus, application of the particulate repellant comprising 60 vol. % glycerin and 40 vol. % aluminum acetate topical solution to the teeth prior to meals effectively inhibits food particulates from adhering to the teeth. Moreover, should any particles stick to the teeth, a glass of water, swished orally, permits the easy and undetectable removal of such particles from the teeth.

In yet another preferred embodiment of the present invention, the solution comprises a mixture of aluminum acetate topical solution, glycerin and a flavoring agent for use as a saliva substitute. The solution of this embodiment will preferably comprise a mixture of equal volumes of aluminum acetate topical solution and glycerin, plus a small volume amount of a flavoring agent, all components being in liquid form. Further, the solution of this embodiment, as well as the solutions in the embodiments discussed above, are relatively, if not completely, transparent liquids. Such solutions are not emulsions.

As an example, approximately eight ounces of the solution can be made by mixing about 120 mL of aluminum acetate topical solution with about 120 mL of glycerin and about 5 mL of lemon extract used as the flavoring agent. The solution of the present invention useful as a saliva substitute preferably contains in the range from about 44 vol. % to about 60 vol. %, more preferably from about 44 vol. % to about 54 vol. %, and most preferably about 49 vol. % aluminum acetate topical solution. The solution of this embodiment of the present invention also preferably contains in the range from about 39 vol. % to about 54 vol. more preferably from about 44 vol. % to about 52 vol. %, and most preferably about 49 vol. % glycerin.

In terms of weight percentages, the solution of the present invention useful as a saliva substitute preferably contains in the range from about 34 wt. % to about 48 wt. %, more preferably from about 38 wt. % to about 43 wt. %, and most preferably about 38.5 wt. % aluminum acetate topical solution. The solution of this embodiment of the present invention also preferably contains in the range from about 50 wt. % to about 64 wt. %, more preferably from about 55 wt. % to about 60 wt. %, and most preferably about 59.5 wt. % glycerin.

The flavoring agent or agents will be present in an amount depending on the individual agent(s) selected, but, if present, will preferably be in the range of about 1 vol. % to about 21 vol. %, more preferably about 2 vol. % to about 6 vol. %, and most preferably about 2 vol. % of the solution. The preferred flavoring agent is a lemon extract which, in addition to providing flavor to the solution, also acts to stimulate natural salivation. In terms of weight percentages, the flavoring agent preferably comprises from about 1 wt. % to about 19 wt. %, more preferably from about 2 wt. % to about 6 wt. %, and most preferably about 2 wt. % of the solution.

Additional flavoring agents are optional, as the incorporation of the lemon extract (or other citric and/or ascorbic acids) into the saliva substitute will, in the absence of any such additional flavoring agents, provide a pleasant, citrus flavor. Additional flavoring agents may include other natural or artificial flavors, e.g., mint oils such as peppermint, wintergreen (methyl salicylate), spearmint, eucalyptus, etc., citrus extracts such as orange extract, lime extract, grapefruit extract, fruit essences such as apple essence, peach essence, raspberry essence and the like. Various synthetic flavors may also be incorporated into the solution. The extracts described above for use as flavoring agents in the saliva substitute of the present invention may include alcohol based extracts, including an alcohol based lemon extract.

The most preferred embodiment of the solution of the present invention useful as a saliva substitute comprises about 49 vol. % glycerin, about 49 vol. % aluminum acetate topical solution and about 2 vol. % lemon extract. In terms of weight percentages, this most preferred embodiment comprises about 59.5 wt. % glycerin, about 38.5 wt. % aluminum acetate topical solution and about 2 wt. % lemon extract.

Examples of other preferred embodiments of the solution of the present invention which have been found to be effective as a saliva substitute include, but are not limited to, the following solutions, comprising:

(1) 39 vol. % glycerin, 59 vol. % aluminum acetate topical solution and 2 vol. % lemon extract;
(2) 44 vol. % glycerin, 54 vol. % aluminum acetate topical solution and 2 vol. % lemon extract;
(3) 54 vol. % glycerin, 44 vol. % aluminum acetate topical solution and 2 vol. % lemon extract;
(4) 50 wt. % glycerin, 48 wt. % aluminum acetate topical solution and 2 wt. % lemon extract;
(5) 55 wt. % glycerin, 43 wt. % aluminum acetate topical solution and 2 wt. % lemon extract; and
(6) 64 wt. % glycerin, 34 wt. % aluminum acetate topical solution and 2 wt. % lemon extract.

The use of the saliva substitute of the present invention as a gargle, one or more times per day, such as after meals and at bedtime, effectively alleviates the symptoms of xerostomia via a non-systemic pathway. The saliva substitute may also be applied to the mouth and throat through the use of a pump spray bottle. In this manner, the saliva substitute of the present invention is conveniently transportable and may be easily applied to the mouth and throat to alleviate the symptoms of dry mouth.

HUMAN CLINICAL INVESTIGATION

A 29 year-old college professor who commonly experienced laryngitis/pharyngitis as a result of classroom lecturing has used the solution of the present invention as a saliva substitute with excellent results. The saliva substitute of the present invention relieved the professor's oral pain and provided continuous moisturizing properties during the course of her lecturing. The professor's once problematic dry-mouth, laryngitis/pharyngitis symptoms, have completely disappeared since using the product. The professor also uses the product prophylactically prior to lecturing as a gargle.

A 68 year-old retired male with asthma uses a series of inhaler devices which amounts to thirty-two inhalations a day during the working hours. His complaints ranged from dryness of the mouth, oral ulcerations, and a thinning/faintness of his voice. This asthmatic obtained relief from all the aforementioned symptoms from gargling with the saliva substitute of the present invention once daily.

An 80 year-old retired male with chronic obstructive pulmonary disease uses inhalers in addition to a nebulizer and home oxygen. This person has a long history, due to his chronic obstructive pulmonary disease, of mouth dryness which has proceeded to dryness/cracking of the lip regions as well as faintness of voice. Previously, this person had used many other products to allay his complaints, including Salivart ® and other synthetic saliva substitutes, all however, to no avail. The saliva substitute of the present invention has corrected this octogenarian's problem of lack of oral moisture and has lasted longer than any other product he has tried.

A 30 year-old professional vocalist and part-time student has used tile saliva substitute of the present invention packaged in a pump-spray bottle for the treatment of a sore throat. She has found that the saliva substitute worked very well and required only a few doses in relieving her sore throat.

It will be understood by those skilled in the art who have the benefit of this disclosure that many variations of the above formulations are possible and that the spirit and scope of the present invention will be limited only by the following claims.

I claim:

1. A composition consisting essentially of aluminum acetate topical solution and glycerin.

2. The composition of claim 1 further consisting essentially of a flavoring agent.

3. The composition of claim 2 wherein the flavoring agent comprises a lemon extract.

4. A composition consisting essentially of:
 (a) from about 39 vol. % to about 60 vol. % glycerin; and
 (b) from about 40 vol. % to about 61 vol. % aluminum acetate topical solution.

5. The composition of claim 4 further comprising a flavoring agent.

6. The composition of claim 5 wherein the flavoring agent con, rises from about 1 vol. % to about 20 vol. % of said solution.

7. The composition of claim 5 wherein the flavoring agent comprises from about 2 vol. % to about 6 vol. % of said solution.

8. The composition of claim 7 wherein the flavoring agent comprises a lemon extract.

9. The composition of claim 6 wherein the flavoring agent comprises a lemon extract.

10. The composition of claim 5 wherein the flavoring agent comprises a lemon extract.

11. The composition of claim 7 wherein glycerin and aluminum acetate topical solution each comprise from about 47 vol. % to about 49 vol. % of said solution.

12. The composition of claim 8 wherein glycerin and aluminum acetate topical solution each comprise from about 47 vol. % to about 49 vol. % of said solution.

13. The composition of claim 7 comprising about 49 vol. % glycerin, about 49 vol. % aluminum acetate topical solution and about 2 vol. % flavoring agent.

14. The composition of claim 8 comprising about 49 vol. % glycerin, about 49 vol. % aluminum acetate topical solution and about 2 vol. % lemon extract.

15. The composition of claim 4 comprising about 50 vol. % glycerin and about 50 vol. % aluminum acetate topical solution.

16. The composition of claim 4 comprising about 60 vol. % glycerin and about 40 vol. % aluminum acetate topical solution.

17. A composition consisting essentially of:
    (a) from about 50 wt. % to about 72 wt. % glycerin; and
    (b) from about 28 wt. % to about 50 wt. % aluminum acetate topical solution.

18. The composition of claim 17 comprising from about 60 wt. % to about, 63 wt. % glycerin and from about 37 wt. % to about 40 wt. % aluminum acetate topical solution.

19. The composition of claim 17 comprising from about 69 wt. % to about 72 wt. % glycerin and from about 28 wt. % to about 31 wt. % aluminum acetate topical solution.

20. The composition of claim 17 further comprising a flavoring agent.

21. The composition of claim 20 wherein the flavoring agent comprises from about 1 wt. % to about 19 wt. % of said solution.

22. The composition of claim 20 wherein the flavoring agent comprises from about 2 wt. % to about 6 wt. % of said solution.

23. The composition of claim 22 wherein the flavoring agent comprises a lemon extract.

24. The composition of claim 21 wherein the flavoring agent comprises a lemon extract.

25. The composition of claim 20 wherein the flavoring agent comprises a lemon extract.

26. The composition of claim 22 comprising from about 57 wt. % to about 59.5 wt. % glycerin and from about 37 wt. % to about 38.5 wt. % aluminum acetate topical solution.

27. The composition of claim 23 comprising from about 57 wt. % to about 59.5 wt. % glycerin and from about 37 wt. % to about 38.5 wt. % aluminum acetate topical solution.

28. The composition of claim 22 comprising about 59.5 wt. % glycerin, about 38.5 wt. % aluminum acetate topical solution and about 2 wt. % flavoring agent.

29. The composition of claim 23 comprising about 59.5 wt. % glycerin, about 38.5 wt. % aluminum acetate topical solution and about 2 wt. % lemon extract.

* * * * *